(12) United States Patent
Karamanoglu et al.

(10) Patent No.: US 7,935,062 B2
(45) Date of Patent: May 3, 2011

(54) DERIVATION OF FLOW CONTOUR FROM PRESSURE WAVEFORM

(75) Inventors: Mustafa Karamanoglu, Fridley, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1102 days.

(21) Appl. No.: 11/045,574

(22) Filed: Jan. 27, 2005

(65) Prior Publication Data

US 2006/0173248 A1    Aug. 3, 2006

(51) Int. Cl.
*A61B 5/02* (2006.01)

(52) U.S. Cl. ............... 600/504; 600/485; 600/526

(58) Field of Classification Search .......... 600/485–507, 600/526

See application file for complete search history.

(56) References Cited

U.S. PATENT DOCUMENTS

| | | | |
|---|---|---|---|
| 4,562,843 A * | 1/1986 | Djordjevich et al. ......... 600/485 |
| 4,802,481 A | 2/1989 | Schroeppel et al. |
| 5,241,966 A | 9/1993 | Finkelstein et al. |
| 5,289,823 A * | 3/1994 | Eckerle ......................... 600/492 |
| 5,400,793 A * | 3/1995 | Wesseling ..................... 600/485 |
| 5,564,434 A | 10/1996 | Halperin et al. |
| 5,797,395 A | 8/1998 | Martin |
| 6,010,457 A * | 1/2000 | O'Rourke ..................... 600/500 |
| 6,071,244 A | 6/2000 | Band et al. |
| 6,250,309 B1 | 6/2001 | Krichen et al. |
| 6,258,035 B1 * | 7/2001 | Hoeksel et al. ............... 600/481 |
| 6,331,162 B1 | 12/2001 | Mitchell |
| 6,394,958 B1 | 5/2002 | Bratteli et al. |
| 6,438,408 B1 | 8/2002 | Mulligan et al. |
| 6,497,655 B1 | 12/2002 | Linberg et al. |
| 2003/0135124 A1 | 7/2003 | Russell |
| 2004/0088123 A1 | 5/2004 | Ji |

FOREIGN PATENT DOCUMENTS

WO    WO2004091378 A    10/2004

* cited by examiner

*Primary Examiner* — Patricia C Mallari
(74) *Attorney, Agent, or Firm* — Michael C. Soldner

(57) ABSTRACT

The present invention provides a system and method for estimating a blood flow waveform contour from a pressure signal. An arterial or ventricular pressure signal is acquired from a pressure sensor. Landmark points are identified on the pressure waveform that correspond to features of a flow waveform. In one embodiment, the landmark pressure waveform points correspond to the onset of flow, the peak flow, and the end of the systolic ejection phase. The landmark pressure waveform points define a contour that approximates the flow contour. Beat-by-beat flow contour estimation can be performed to allow computation of flow-related hemodynamic parameters such as stroke volume or cardiac output for use in patient monitoring and/or therapy management.

10 Claims, 7 Drawing Sheets

DERIVATION OF FLOW CONTOUR FROM PRESSURE WAVEFORM

FIELD OF THE INVENTION

The present invention relates generally to hemodynamic monitoring devices and methods and particularly to a method and apparatus for deriving a blood flow contour from a pressure waveform.

BACKGROUND OF THE INVENTION

Implantable hemodynamic monitors are available for monitoring right ventricular pressure chronically in an ambulatory patient. Patients with congestive heart failure (CHF) have elevated cardiac filling pressures and reduced cardiac output. A major treatment objective is to lower filling pressures while maintaining adequate cardiac output. Therefore, from a hemodynamic monitoring perspective, it is advantageous to monitor both filling pressures and measures of cardiac output.

Chronic pressure monitoring in ambulatory patients using chronically implantable pressure sensors has been realized. However, direct monitoring of flow chronically in an ambulatory patient has not been realized clinically. Pressure measurements alone do not account for variations in vascular impedance, which changes in response to varying physiological conditions and is time-varying over the cardiac cycle. Variations in vascular impedance will affect the forward arterial flow produced by developed pressure in the ventricles. Pressure pulse contour cardiac output methods have been developed for estimating flow from arterial pressure signals, however, such methods generally require frequent calibration, particularly after a suspected change in hemodynamics.

BRIEF SUMMARY OF THE INVENTION

The present invention provides a system and method for estimating a blood flow waveform contour from a pressure signal. The estimated flow contour is useful for estimating forward flow (cardiac output) and useful in monitoring changes in vascular impedance or other hemodynamic parameters.

In one embodiment, the system includes a pressure sensor adapted for implantation in an anatomical location suitable for acquiring a ventricular or arterial pressure signal. The pressure sensor is coupled to an implantable cardiac monitoring device having control circuitry, in the form of a microprocessor, and associated memory for acquiring and storing pressure signals. The device will typically include a cardiac electrogram (EGM) sensing circuit to allow for the detection of the onset of cardiac cycles or the R-wave. R-wave detection can be used for timing pressure data acquisition during the desired portion of the cardiac cycle, for example during the systolic phase and in particular the systolic ejection phase, or during the diastolic phase and in particular the early diastolic filling phase. The pressure signals are processed by the microprocessor to estimate the flow contour on a beat-by-beat basis when flow monitoring is enabled. The implantable cardiac monitoring device is equipped with telemetry circuitry for communicating with an external programmer. Pressure and flow data may be uplinked to the external programmer and further processed by a microprocessor included in the external programmer or transferred to another computer for further analysis.

In other embodiments, the system includes an implantable pressure sensor and an ECG or EGM sensing circuit interfaced with an external monitoring device. The external monitoring device includes a microprocessor and associated memory for storing the pressure and ECG/EGM data for processing pressure signals to estimate the flow contour.

In still other embodiments, high-fidelity pressure signals are obtained from external pressure sensors positioned for sensing an arterial pressure signal and coupled to an external monitoring device having processing circuitry for receiving and processing the pressure signals.

In an associated method for deriving a flow contour from a pressure signal, landmark points are identified on the pressure signal contour that correspond to features of the flow contour. The flow contour is observed to be substantially unchanged in response to clinical interventions that change afterload, preload, or cardiac contractility. The pressure signal can be substantially altered in response to the same intervention, however, selected points on the pressure waveform can be identified which correspond in time to features of the flow contour. The flow contour can be approximated by defining a contour based on landmark points on the pressure signal that correspond to features of the actual flow contour.

In one embodiment, the landmark points identified for use in estimating the flow contour from an arterial pressure signal include the onset of the pressure rise, a first pressure peak, and the time of the dicrotic notch. These landmark pressure waveform points correspond to the onset of flow, the peak flow, and the end of the systolic ejection phase, respectively. The three landmark points define a triangle which can be used to approximate the flow contour.

In another embodiment, an arterial flow contour is derived from a ventricular pressure waveform. In one example, landmark points identified from a right ventricular pressure waveform that correspond to features of the pulmonary artery flow contour include the pressure amplitude at the time of the peak rate in pressure rise (dP/dt max), an early shoulder in the pressure waveform that corresponds to an inflection point in the first derivative of the pressure signal, and the pressure amplitude at the time of dP/dt min. These landmark points correspond to the onset of flow, the peak flow, and the end of ejection and define a triangle that can be used to approximate the flow contour.

Alternative embodiments can include substitution or addition of selected landmark points corresponding to actual flow contour features. The estimated flow contour may be used for estimating stroke volume, forward flow or cardiac output, vascular resistance, characteristic impedance, wave reflection, contractility, or other hemodynamic parameters of interest that normally rely on flow measurements.

DETAILED DESCRIPTION

Figure 1:
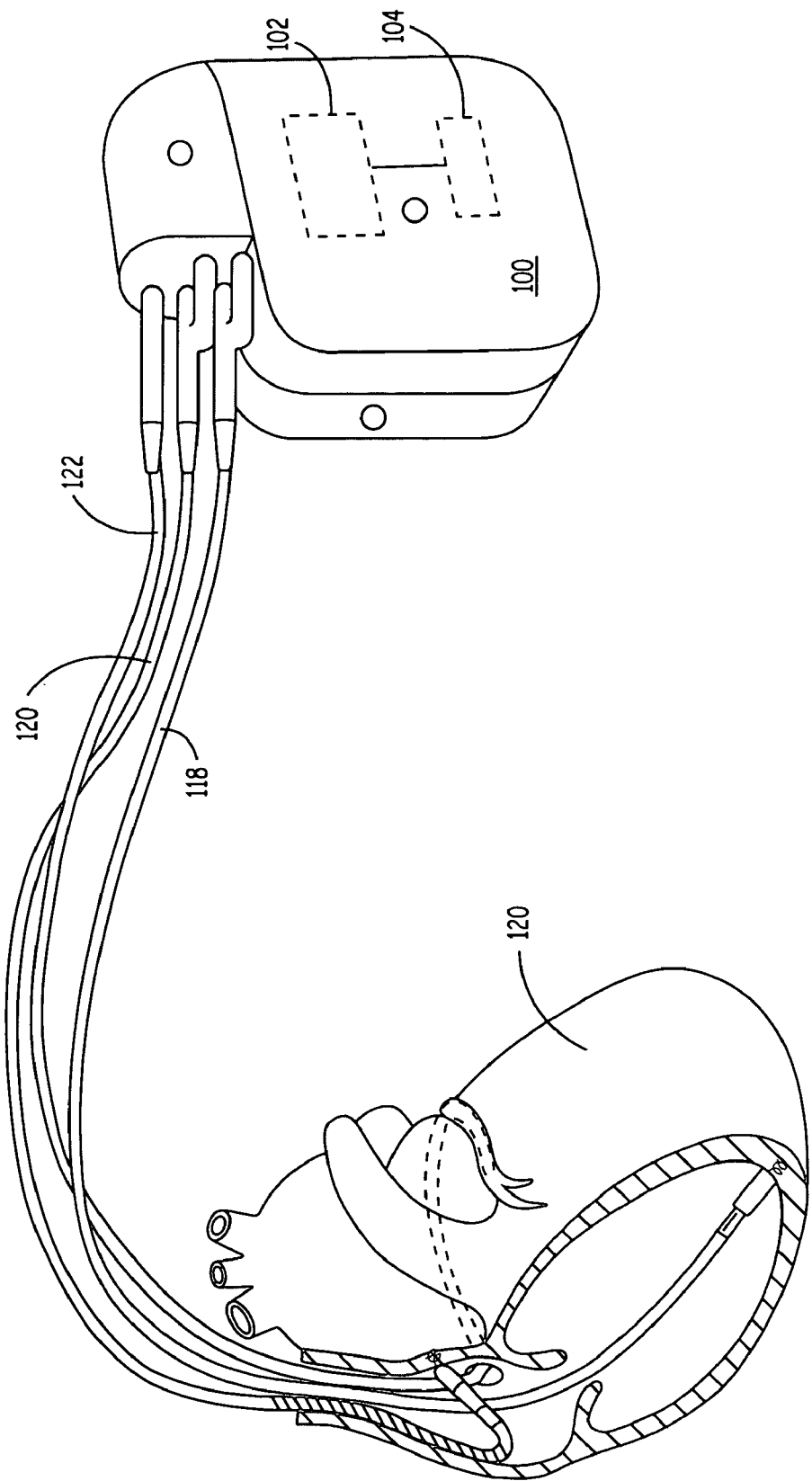
FIG. 1 is an illustration of an exemplary implantable medical device (IMD) connected to monitor a patient's heart.

FIG. 1 is an illustration of an exemplary implantable medical device (IMD) 100 connected to monitor a patient's heart 120. IMD 100 may be configured to integrate both monitoring and therapy features, as will be described below. IMD 100 collects and processes data about heart 120 from one or more sensors including a pressure sensor and an electrode pair for sensing cardiac electrogram (EGM) signals. IMD 100 may further provide therapy or other response to the patient as appropriate, and as described more fully below. As shown in FIG. 1, IMD 100 may be generally flat and thin to permit subcutaneous implantation within a human body, e.g., within upper thoracic regions or the lower abdominal region. IMD 100 is provided with a hermetically-sealed housing that encloses a processor 102, a digital memory 104, and other components as appropriate to produce the desired functionalities of the device. In various embodiments, IMD 100 is implemented as any implanted medical device capable of measuring the heart rate of a patient and a ventricular or arterial pressure signal, including, but not limited to a pacemaker, defibrillator, electrocardiogram monitor, blood pressure monitor, drug pump, insulin monitor, or neurostimulator. An example of a suitable IMD that may be used in various exemplary embodiments is the CHRONICLE® monitoring device available from Medtronic, Inc. of Minneapolis, Minn., which includes a mechanical sensor capable of detecting a pressure signal. In a further embodiment, IMD 100 is any device that is capable of sensing a pressure signal and providing pacing and/or defibrillation or other electrical stimulation therapies to the heart. Another example of an IMD capable of sensing pressure-related parameters is described in commonly assigned U.S. Pat. No. 6,438,408B1 issued to Mulligan et al. on Aug. 20, 2002.

Processor 102 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 102 executes instructions stored in digital memory 104 to provide functionality as described below. Instructions provided to processor 102 may be executed in any manner, using any data structures, architecture, programming language and/or other techniques. Digital memory 104 is any storage medium capable of maintaining digital data and instructions provided to processor 102 such as a static or dynamic random access memory (RAM), or any other electronic, magnetic, optical or other storage medium.

As further shown in FIG. 1, IMD 100 may receive one or more cardiac leads for connection to circuitry enclosed within the housing. In the example of FIG. 1, IMD 100 receives a right ventricular endocardial lead 118, a left ventricular coronary sinus lead 122, and a right atrial endocardial lead 120, although the particular cardiac leads used will vary from embodiment to embodiment. In addition, the housing of IMD 100 may function as an electrode, along with other electrodes that may be provided at various locations on the housing of IMD 100. In alternate embodiments, other data inputs, leads, electrodes and the like may be provided. Ventricular leads 118 and 122 may include, for example, pacing electrodes and defibrillation coil electrodes (not shown) in the event IMD 100 is configured to provide pacing, cardioversion and/or defibrillation. In addition, ventricular leads 118 and 122 may deliver pacing stimuli in a coordinated fashion to provide biventricular pacing, cardiac resynchronization, extra systolic stimulation therapy or other therapies. IMD 100 obtains pressure data input from a pressure sensor that is carried by a lead such as right ventricular endocardial lead 118. IMD 100 may also obtain input data from other internal or external sources (not shown) such as an oxygen sensor, pH monitor, accelerometer or the like.

In operation, IMD 100 obtains data about heart 120 via leads 118, 120, 122, and/or other sources. This data is provided to processor 102, which suitably analyzes the data, stores appropriate data in memory 104, and/or provides a response or report as appropriate. Any identified cardiac episodes (e.g. an arrhythmia or heart failure decompensation) can be treated by intervention of a physician or in an automated manner. In various embodiments, IMD 100 activates an alarm upon detection of a cardiac event. Alternatively or in addition to alarm activation, IMD 100 selects or adjusts a therapy and coordinates the delivery of the therapy by IMD 100 or another appropriate device. Optional therapies that may be applied in various embodiments may include drug delivery or electrical stimulation therapies such as cardiac pacing, resynchronization therapy, extra systolic stimulation, neurostimulation.

Figure 2:
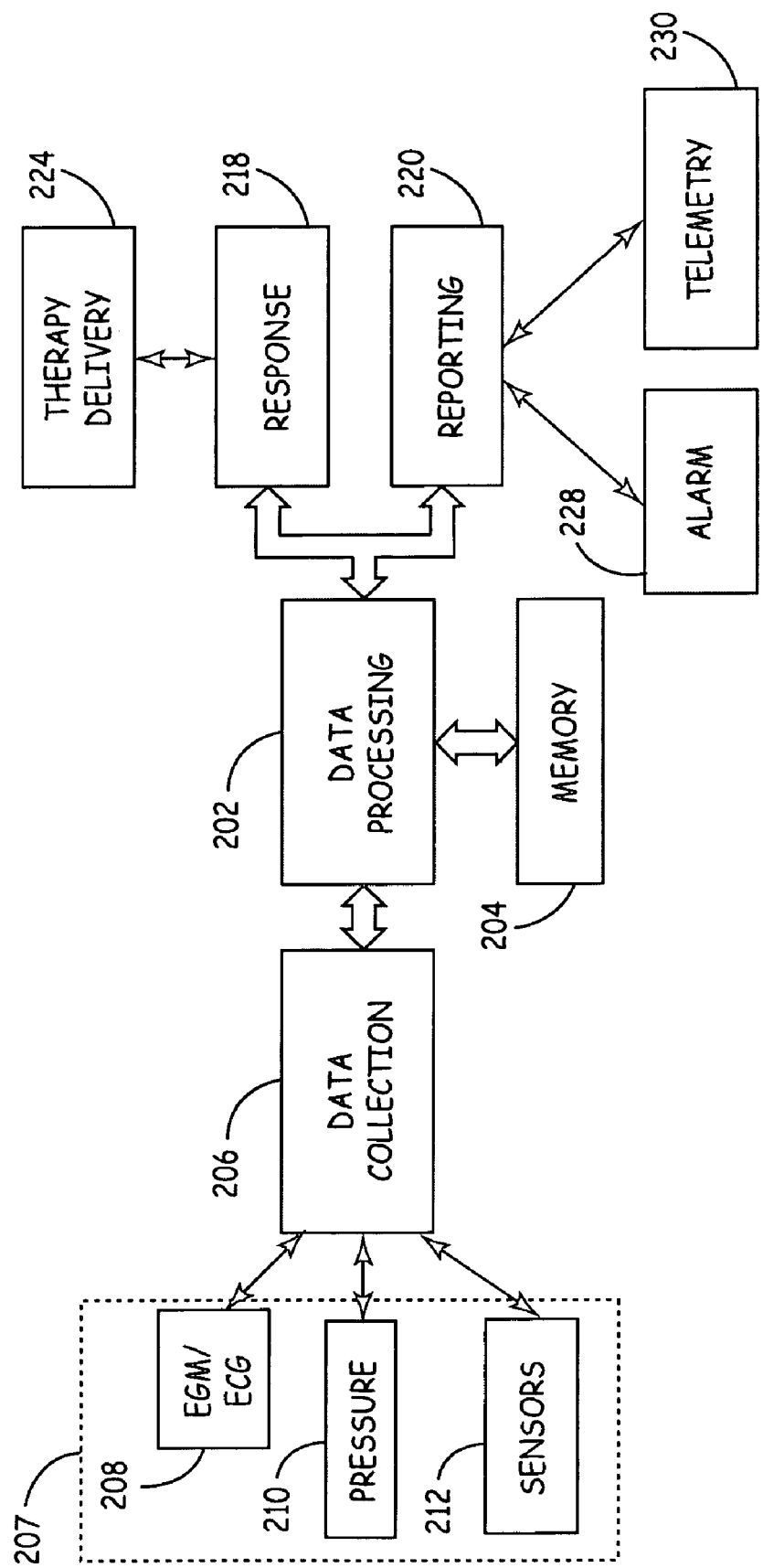
FIG. 2 is a block diagram summarizing the data acquisition and processing functions appropriate for practicing the invention.

FIG. 2 is a block diagram summarizing the data acquisition and processing functions appropriate for practicing the invention. The functions shown in FIG. 2 may be implemented in an IMD system, such as IMD 100 shown in FIG. 1. Alternatively, the functions shown in FIG. 2 may be implemented in an external monitoring system that includes sensors coupled to a patient for acquiring pressure signal data. The system includes a data collection module 206, a data processing module 202, a response module 218 and/or a reporting module 220. Each of the various modules may be implemented with computer-executable instructions stored in memory 104 and executing on processor 102 (shown in FIG. 1), or in any other manner.

The exemplary modules and blocks shown in FIG. 2 are intended to illustrate one logical model for implementing an IMD 100, and should not be construed as limiting. Indeed, the various practical embodiments may have widely varying software modules, data structures, applications, processes and the like. As such, the various functions of each module may in practice be combined, distributed or otherwise differently-organized in any fashion across a patient monitoring system. For example, a system may include an implantable pressure sensor and EGM circuit coupled to an IMD used to acquire pressure and EGM data, an external device in communication with the IMD to retrieve the pressure and EGM data and coupled to a communication network for transferring the pressure and EGM data to a remote patient management center for analysis. Examples of remote patient monitoring systems in which aspects of the present invention could be implemented are generally disclosed in U.S. Pat. No. 6,497,655 issued to Linberg and U.S. Pat. No. 6,250,309 issued to Krichen et al., both of which patents are incorporated herein by reference in their entirety.

Data collection module 206 is interfaced with one or more data sources 207 to obtain data about the patient. Data sources 207 include any source of information about the patient's heart or other physiological signals. Data sources 207 include an ECG or EGM source 208 that provides cardiac electrical signals such as P-waves or R-waves used to monitor the patient's heart rhythm. Data sources 207 further include a pressure sensor 210 for obtaining a pressure signal from which a flow contour will be approximated according to methods described in detail below.

Pressure sensor 210 may be deployed in an artery for measuring an arterial pressure signal or in the left or right ventricle for measuring a ventricular pressure signal. In some embodiments, pressure sensor 210 may include multiple pressure sensors deployed at different arterial and/or ventricular sites to provide multiple pressure waveforms for use in estimating a flow contour. Pressure sensor 210 may be embodied as the pressure sensor disclosed in commonly assigned U.S. Pat. No. 5,564,434, issued to Halperin et al., hereby incorporated herein in its entirety.

Data sources 207 may include other sensors 212 for acquiring physiological signals useful in monitoring a cardiac condition such as an accelerometer or wall motion sensor, a blood gas sensor such as an oxygen sensor, a pH sensor, or impedance sensors for monitoring respiration, lung wetness, or cardiac chamber volumes. The various data sources 207 may be provided alone or in combination with each other, and may vary from embodiment to embodiment.

Data collection module 206 receives data from each of the data sources 207 by polling each of the sources 207, by responding to interrupts or other signals generated by the sources 207, by receiving data at regular time intervals, or according to any other temporal scheme. Data may be received at data collection module 206 in digital or analog format according to any protocol. If any of the data sources generate analog data, data collection module 206 translates the analog signals to digital equivalents using an analog-to-digital conversion scheme. Data collection module 206 may also convert data from protocols used by data sources 207 to data formats acceptable to data processing module 202, as appropriate.

Data processing module 202 is any circuit, programming routine, application or other hardware/software module that is capable of processing data received from data collection module 206. In various embodiments, data processing module 202 is a software application executing on processor 102 of FIG. 1 or another external processor to implement the process described below in conjunction with FIG. 3. Accordingly, data processing module 202 processes pressure signals for estimating a flow contour, as described more fully below.

In an exemplary embodiment, processing module 202 receives data from pressure sensor 210 and EGM data from EGM sensing electrodes 208 from data collection module 206 and interprets the data using analog or digital signal processing techniques to approximate a flow contour on a beat-by-beat basis. The estimated flow contour can be used further to compute an estimated stroke volume, cardiac output, vascular resistance or other hemodynamic monitoring parameters of interest that require a measure of blood flow. The estimated flow contour and/or intermediate computational results may be stored in memory 204, which may correspond to hardware memory 104 shown in FIG. 1, or may be implemented with any other available digital storage device.

When a change in hemodynamic function based on the estimated flow contour and/or other hemodynamic signals is detected, processing module 202 may trigger an appropriate response. Responses may be activated by sending a digital message in the form of a signal, passed parameter or the like to response module 218 and/or reporting module 220.

Reporting module 220 is any circuit or routine capable of producing appropriate feedback from the IMD to the patient or to a physician. In various embodiments, suitable reports might include storing data in memory 204, generating an audible or visible alarm 228, producing a wireless message transmitted from a telemetry circuit 230. Reports may include information about the estimated flow contour or hemodynamic parameters derived from the flow contour, pressure measurements derived from the pressure signal, heart rhythm, time and date of data collection, and any other appropriate data. In a further embodiment, the particular response provided by reporting module 220 may vary depending upon the severity of the hemodynamic change. Minor episodes may result in no alarm at all, for example, or a relatively non-obtrusive visual or audible alarm. More severe episodes might result in a more noticeable alarm and/or an automatic therapy response.

When the functionality diagramed in FIG. 2 is implemented in an IMD, telemetry circuitry 230 is included for communicating data from the IMD to an external device adapted for bidirectional telemetric communication with IMD. The external device receiving the wireless message may be a programmer/output device that advises the patient, a physician or other attendant of serious conditions, e.g., via a display or a visible or audible alarm. Information stored in memory 204 may be provided to an external device to aid in diagnosis or treatment of the patient. Alternatively, the external device may be an interface to a communications network such that the IMD is able to transfer data to an expert patient management center or automatically notify medical personnel if an extreme episode occurs.

Response module 218 is any circuit, software application or other component that interacts with any type of therapy-providing system 224, which may include any type of therapy delivery mechanisms such as a drug delivery system, neurostimulation, and/or cardiac stimulation. In some embodiments, response module 218 may alternatively or additionally interact with an electrical stimulation therapy device that may be integrated with an IMD to deliver pacing, extra systolic stimulation, cardioversion, defibrillation and/or any other therapy. Accordingly, the various responses that may be provided by the system vary from simple storage and analysis of data to actual provision of therapy in various embodiments. Any therapy provided may be controlled or adjusted in response to a hemodynamic change observed as a change in flow estimated from a pressure signal or in response to a combination of physiological signals acquired by data sources 207. Drug dosage may be adjusted according to episode severity, for example, or electrical stimulation parameters can be adjusted in response to observed deterioration in hemodynamic measures.

The various components and processing modules shown in FIG. 2 may be implemented in an IMD 100 (FIG. 1) and housed in a common housing such as that shown in FIG. 1. Alternatively, functional portions of the system shown in FIG. 2 may be housed separately. For example, portions of the therapy delivery system 224 could be integrated with IMD 100 or provided in a separate housing, particularly where the therapy delivery system includes drug delivery capabilities. In this case, response module 218 may interact with therapy delivery system 224 via an electrical cable or wireless link.

Figure 3:
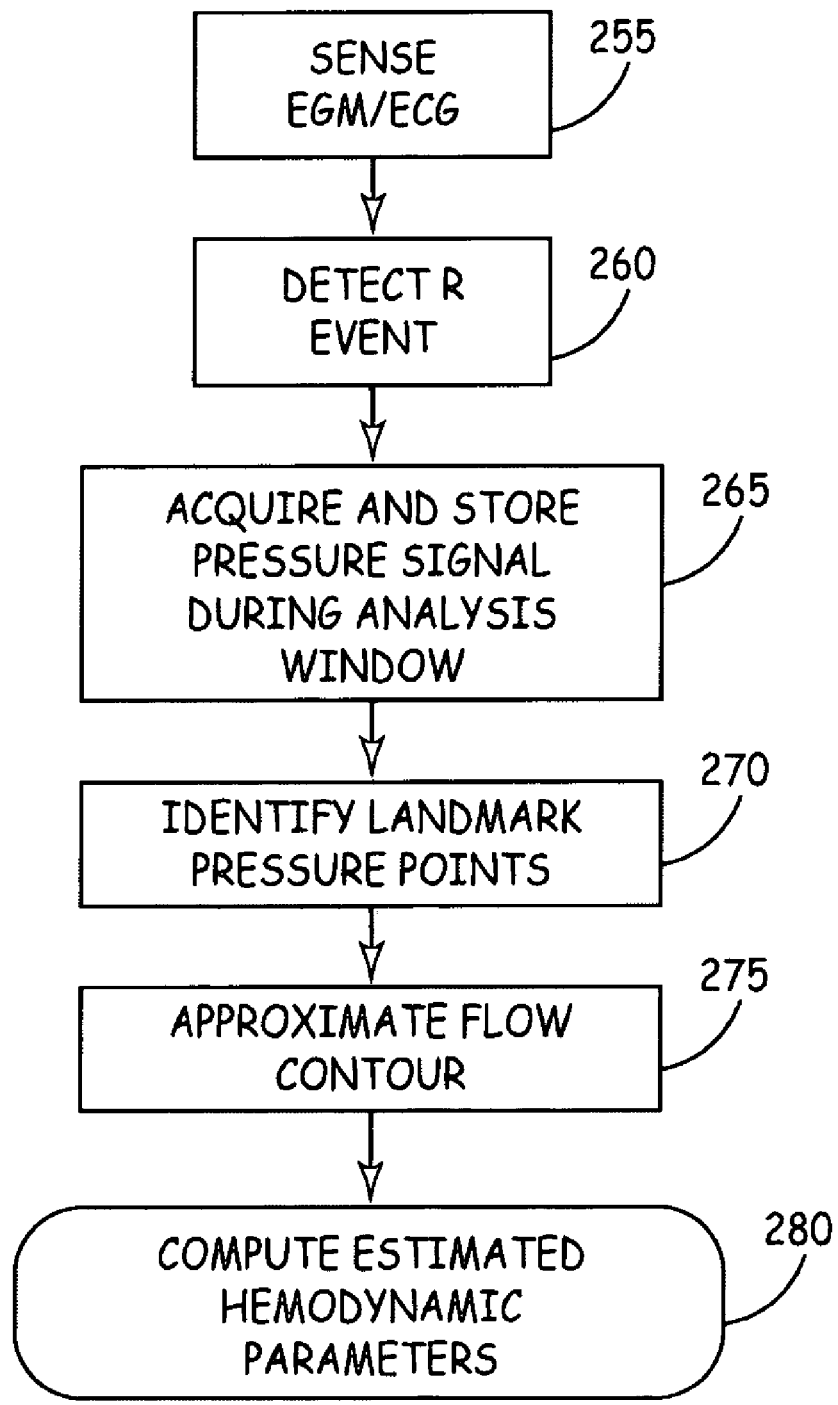
FIG. 3 is a flow chart summarizing a method for estimating a flow contour from a pressure signal.

FIG. 3 is a flow chart summarizing a method for estimating a flow contour from a pressure signal. Pressure signal acquisition for flow monitoring may be enabled upon detecting predetermined triggering events, on a scheduled basis, or manually by a clinician, patient or other caregiver using an external device. When flow monitoring is enabled, the EGM/

ECG signal is sensed at step 255 to allow detection of the onset of a cardiac cycle based on a detected R-wave event at step 260. A detected R-wave event may be an R-wave detected on an EGM/ECG signal but could alternatively be a pacing event or other electrical signal appropriate for marking the start of a cardiac cycle. The present invention is not limited, however, to the use of an EGM/ECG signal or pacing signal for detecting the start of a cardiac cycle. Other physiological signals could be substituted from which an approximation of the start of the cardiac cycle may be made. In one alternative embodiment, a pressure signal may be used to detect the start of the cardiac cycle. For example, a predetermined threshold crossing of amplitude or dP/dt may be detected as an R-wave related event and used as the starting point of a cardiac cycle for the purposes of the present invention.

Once an R-wave event is detected at step 260, the pressure signal is acquired for a predetermined interval of time during which analysis of the pressure signal will be performed for estimating the corresponding flow contour. The pressure signal data is stored in a memory buffer to allow the signal to be analyzed during the analysis window defined by the predetermined interval of time. The analysis window is defined such that the systolic portion of the cardiac signal is included to allow the systolic phase of the flow contour to be approximated. In one embodiment, pressure signal data is stored in a memory buffer for about 500 msec following an R-wave event detection. Anomalous cardiac cycles associated with arrhythmias, premature contractions, or noise may be rejected.

At step 270, a number of landmark pressure points are identified from the pressure signal during the analysis window. As will be described in detail below, the amplitude or time of the landmark pressure points will be used for defining a geometric boundary or area for use in approximating a flow contour at step 275. The flow contour is estimated on a beat-by-beat basis and results may be statistically analyzed over time to obtain baseline, mean, trends, ranges or other statistical parameters of the beat-by-beat flow contour estimate.

At step 280, any of a number of hemodynamic parameters that require a measure of flow can be computed using the estimated flow contour. Such parameters include, for example, stroke volume (SV), cardiac output (CO), vascular resistance, characteristic impedance, contractility, and wave reflection. In one embodiment, the estimated flow contour is used to compute an estimated beat-by-beat stroke volume (SV) measurement using the area defined by the estimated flow contour. Using heart rate information obtained from the EGM/ECG signal, the SV measurements can be used to compute an estimate of cardiac output (CO). The estimated CO may be computed on a beat-by-beat or interval basis allowing trends in CO to be determined by data processing circuitry 202 (FIG. 2). Changes in estimated CO detected by data processing circuitry 202 can be responded to appropriately by response module 218 (FIG. 2). Thus, estimated flow contour data may be used in a closed-loop control algorithm for controlling therapy delivery. Estimated flow contour data may additionally or alternatively be stored in IMD memory for uplinking to an external device for offline review and analysis by a clinician.

Upon uplinking to an external device, the estimated flow contour data provided in digital units may be converted to units of volume. CO may then be determined in units of volume per unit time, and other hemodynamic parameters computed using the flow contour estimate may be converted to appropriate physical units. The estimated flow contour values are converted to units of volume by multiplying by a calibration gain and/or adding a calibration offset value. The calibration values are determined for a given pressure sensor and may be individualized for a given patient. In some embodiments, non-linear calibration factors may be used for converting estimated flow contour digital values to actual values in units of volume.

Figure 4:
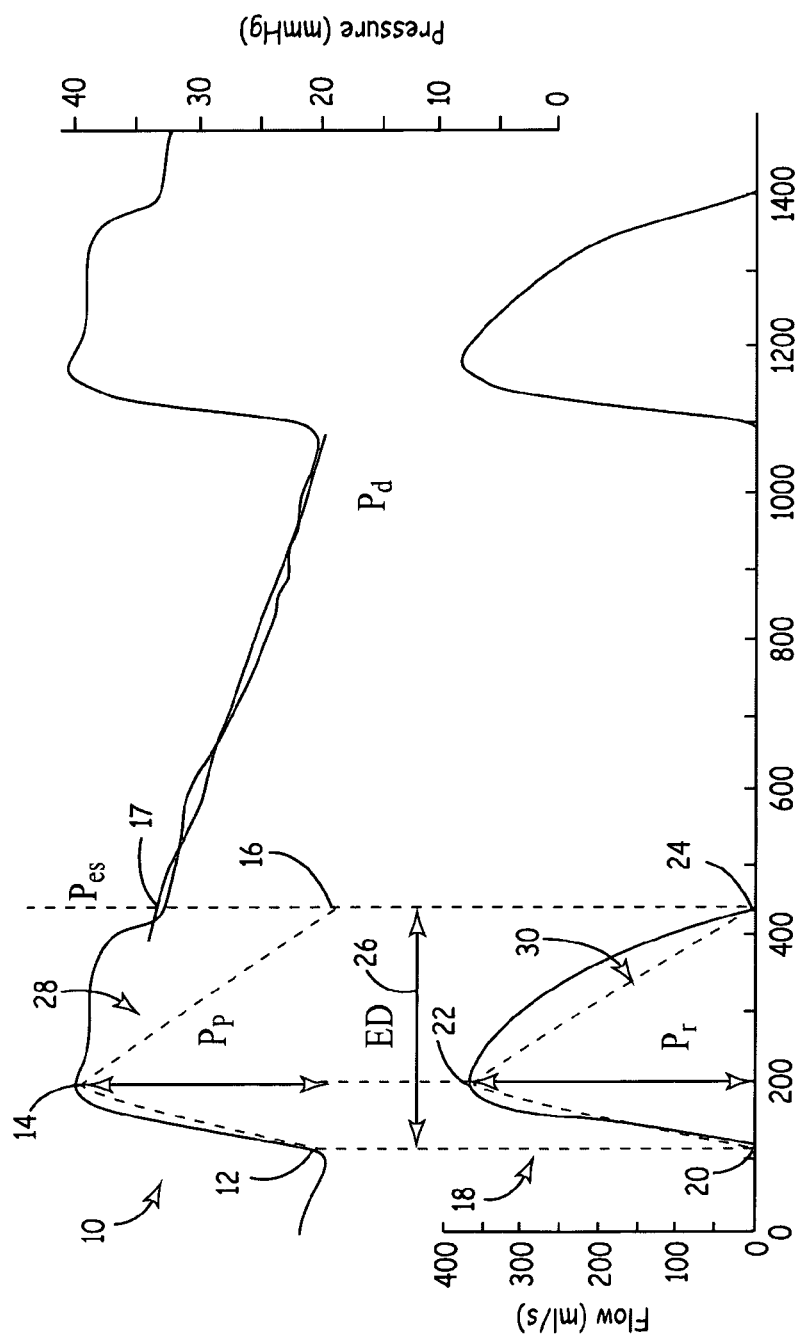
FIG. 4 is a time-based plot of an arterial pressure signal and a flow signal and illustrates one method for estimating a flow contour from the arterial pressure signal.

FIG. 4 is a time-based plot of an arterial pressure signal and a flow signal and illustrates one method for estimating a flow contour from the arterial pressure signal. In this example, a pulmonary artery pressure (PAP) signal 10 is acquired for use in approximating a pulmonary flow waveform 18. A recording of the pulmonary flow signal 18 is shown for the purpose of illustrating the usefulness of landmark pressure points determined from the PAP signal 10 in approximating the flow contour, however, during practice of the invention the flow waveform 18 is not obtained during monitoring procedures. The flow waveform 18 may be obtained during calibration procedures for determining calibration constants that can be used to convert digital units to units of volume if desired.

The pulmonary flow contour resembles a triangle 30. The triangle 30 is defined by three landmark points on the flow contour, the onset of flow 20, the peak flow 22, and the end of flow 24 at the end of the systolic ejection duration (ED) 26. This flow contour changes little in response to interventions that alter the pressure contour. By identifying landmark points on the PAP waveform 10 that correspond to the three points 20, 22 and 24 defining flow contour triangle 30, a pressure triangle 28 may be defined that approximates the flow contour.

The onset of PAP development 12 coincides with the onset of pulmonary flow 20. The peak PAP 14 corresponds with the peak flow 22. The time 16 of the dicrotic notch 17 in the PAP waveform 10 corresponds to closure of the pulmonic valve at the end of the systolic ejection duration 26, marking the end of flow 24. A pressure triangle 28 is defined by the landmark pressure points 12, 14 and 16 and can be used to approximate the pulmonary flow contour. As such, characteristics of pressure triangle 28 may be used to derive flow-related data for patient monitoring purposes. In one example, the area of the triangle 28 may be computed as an estimate of stroke volume:

$$SVest = 0.5 * (Pp * ED)$$

wherein Pp is the magnitude of the peak PAP 14 and ED is the ejection duration determined as the time difference between the onset 12 and end 16 of the PAP waveform 10.

Figure 5:
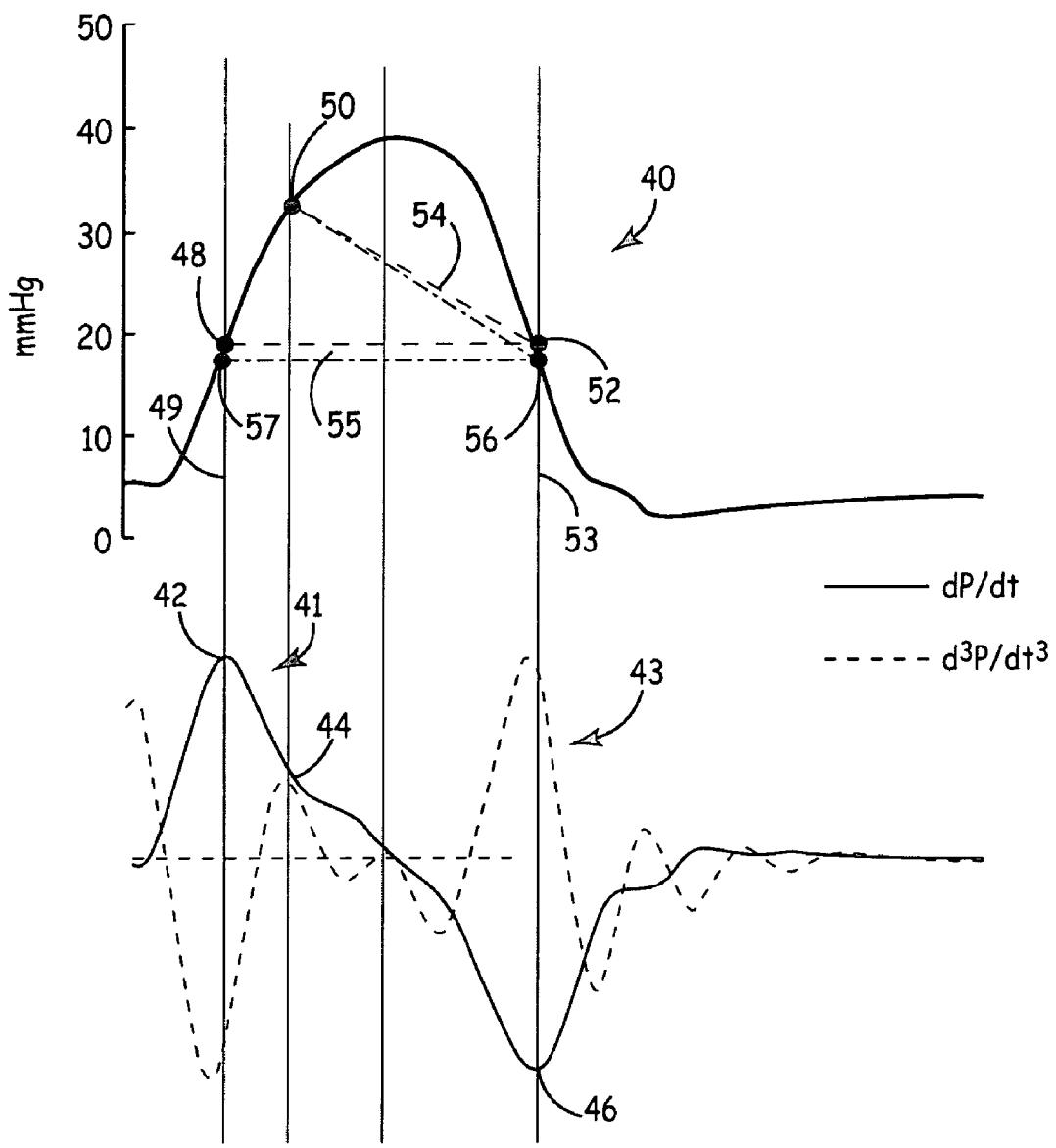
FIG. 5 shows a right ventricular pressure waveform and illustrates a method for estimating the pulmonary artery flow contour from the right ventricular pressure waveform.

FIG. 5 shows a right ventricular pressure waveform and illustrates a method for estimating the pulmonary artery flow contour from a ventricular pressure waveform. Landmark points are selected on the right ventricular pressure (RVP) waveform 40 that correspond to features of the pulmonary flow waveform. The first derivative dP/dt 41 of the RVP signal and the third derivative $d^3P/dt^3$ 43 are also shown to illustrate methods for identifying landmark points on the RVP waveform 40.

In the embodiment shown, a first landmark point 48 is the point on the RVP waveform 40 at the approximate time of pulmonic valve opening and the onset of pulmonary artery flow. The first landmark point 48 is identified as the point on the RVP waveform at the time of the maximum rate of RVP rise, or the peak of the first derivative (dP/dt) 42.

The second landmark point 50 is a point on the RVP waveform at the first shoulder of the RVP waveform 40. The first shoulder on the RVP waveform 40 defining the second landmark point 50 has been observed to correspond in time to peak pulmonary artery flow. The first shoulder on the RVP waveform 40 defining the second landmark point 50 can be identified as the as the point on the RVP waveform 40 at the time of the first peak of the third derivative ($d^3P/dt^3$) 44 that occurs after dP/dt max 42.

A third landmark point 52 corresponds approximately to the time of pulmonic valve closure at the end of the ejection phase and the end of forward flow in the pulmonary artery. In one embodiment, the third landmark point 52 is identified as the point on the descending portion of the RVP waveform 40 that is equal to the RVP amplitude at the first landmark point 48. Having identified three landmark points 48, 50 and 52 on the RVP waveform, which correspond in time to the onset of pulmonary artery flow, peak pulmonary artery flow, and the end of pulmonary artery flow, the pulmonary flow contour can be approximated as a triangle 54 (dashed line) defined by the three landmark points 48, 50, and 52. The base of the triangle 54 is parallel to the absisca.

An alternative triangle 55 (dash-dot line) can be defined using alternatively defined landmark points 50, 56, and 57. Landmark point 50 is defined as described above as the point on the RVP waveform 40 occurring at the time of the first peak of the third time derivative ($d^3P/dt^3$) 44 that occurs after dP/dt max 42. Landmark point 50 corresponds to the first shoulder of the RVP waveform 40. The second landmark point 56 is defined as the point occurring on the RVP waveform at the time of the minimum dP/dt 46 and approximates the time of pulmonic valve closure and the end of flow. The third landmark point 57 is defined as the point occurring on the ascending portion of the RVP waveform 40 equal to the RVP amplitude at landmark point 56. The triangle 55 has a base parallel to the absisca.

In another alternative embodiment, a triangular estimation of the flow contour can be derived as a triangle having a base that is not parallel to the absisa. The base of the triangle (not illustrated in FIG. 5) is defined by the landmark point 48 on the RVP waveform occurring at the time of dP/dtmax 42 and by the landmark point 56 on the RVP waveform corresponding to the time of dP/dtmin 46. The third point of the triangle is defined by landmark point 50 on the RVP waveform 40 at the first shoulder of the waveform 40.

As can be seen by the above examples, a triangular estimation of a flow contour includes selecting three landmark points which are defined by a pressure amplitude derived from the pressure waveform at a time that corresponds in time to a feature of the flow contour being estimated. The landmark points selected may or may not fall exactly on the pressure waveform as in the case of landmark point 52 of triangle 54 and landmark point 57 of triangle 55. The landmark points are defined by: 1) a pressure derived from the pressure waveform at a selected time corresponding to the onset, peak, or end of flow or another feature of the flow contour, and 2) a time corresponding to a feature of the flow contour. The landmark points can be represented in a Cartesian coordinate system as (p,t) where the pressure amplitude, p, is plotted along the y-axis and the time, t, is plotted along the x-axis.

The time used to derive the pressure amplitude of a landmark point and the time at which the landmark point is applied for defining a triangular estimation of the flow contour may not be the same in some embodiments, resulting in a landmark point that does not fall exactly on the RVP waveform 40. In one example, a landmark point may be defined by a pressure amplitude equal to the RVP amplitude at the time of dP/dtmax 42 and by a time of dP/dtmin 46. Such a point will not fall exactly on the RVP waveform 40, but could be used in defining an estimated flow contour.

In alternative embodiments, other pressure signals can be acquired for approximating a other flow contours. For example, left ventricular pressure, aortic pressure, or other arterial pressure signals can be acquired for estimating an arterial flow contour. Having an estimate of the flow contour, a number of useful applications can be implemented for assessing a patient's hemodynamic status. As described previously, the estimated flow contour can be used to estimate stroke volume by computing an area defined by the estimated contour. The beat-by-beat stroke volume is computed from the estimated pulmonary flow contour using the following equation for computing the area of the pressure triangle 54:

$$SV=0.5*(RVP\text{shoulder}-RVP\text{onset})*(T\text{onset}-T\text{end})$$

wherein RVPshoulder is the RVP amplitude at the second landmark point 50, RVPonset is the RVP amplitude at the first landmark point 48, Tonset is the time of the first landmark point 48 and T(end) is the time of the third landmark point 52. In the example of pressure triangle 55 shown in FIG. 5, RVPshoulder is the RVP amplitude at the second landmark point 50, RVPonset is the RVP amplitude at the first landmark point 49, Tonset is the time of the first landmark point 49 and T(end) is the time of the third landmark point 56. In other embodiments, the appropriate values are selected for suitably computing an area of the estimated flow contour as an estimate of SV.

Knowing an estimate of stroke volume, flow or cardiac output, can be computed using a measured heart rate. Other hemodynamic parameters that normally require a flow measurement can be computed using the estimated flow contour such as vascular resistance, characteristic impedance, ventricular contractility, wave reflectance.

Figure 6A:
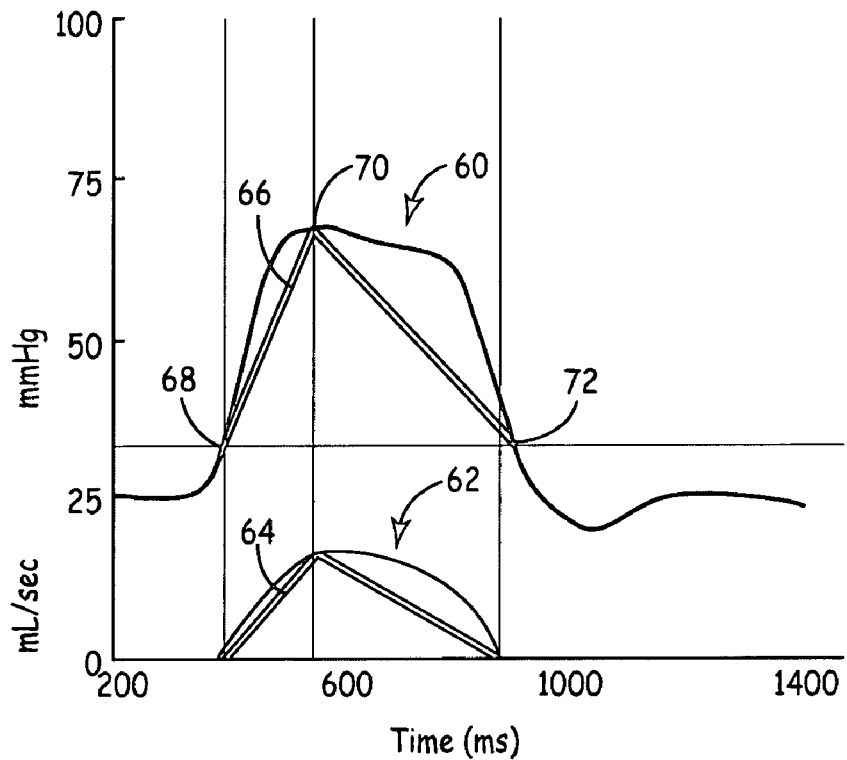
FIG. 6A shows a comparison of pressure derived flow contours and actual flow contours under normal, control conditions.
Figure 6B:
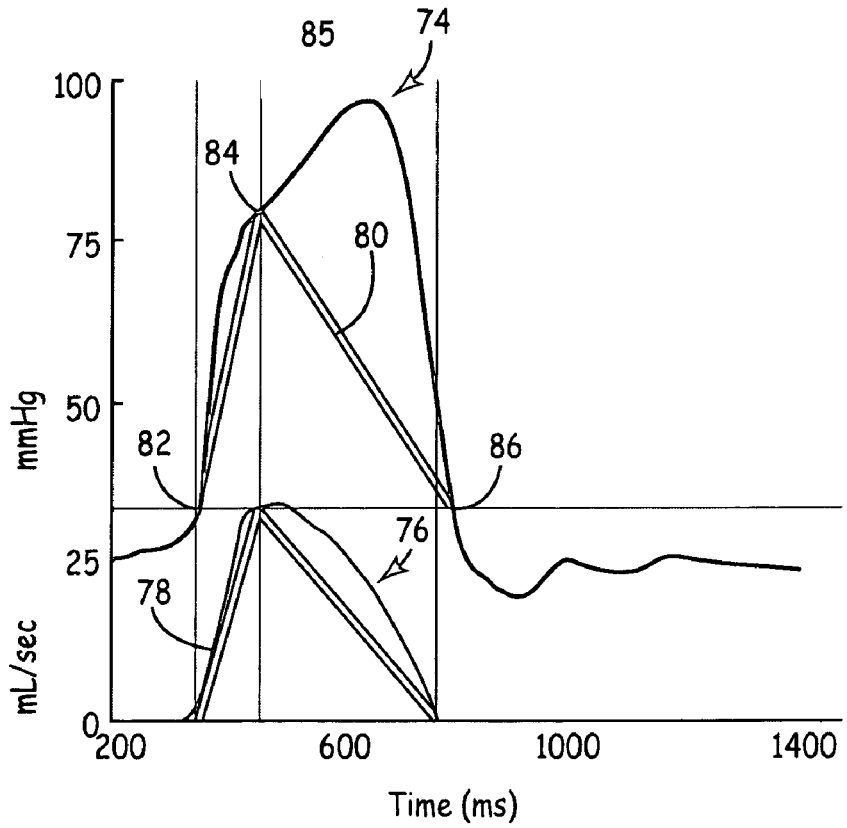
FIG. 6B shows a comparison of pressure derived flow contours and actual flow contours after Dobutamine infusion.

FIGS. 6A and 6B show a comparison of pressure derived flow contours and actual flow contours for control conditions and after Dobutamine infusion. In FIG. 6A, a control RVP waveform 60 and a control pulmonary artery flow waveform 62 obtained during a canine study are shown. The control pulmonary artery waveform 62 is seen to be approximately the shape of a triangle 64. Extraction of landmark points 68, 70 and 72, corresponding in time to the onset, peak and end of pulmonary artery flow, respectively, allows triangular estimation 66 of the flow contour using the method described in conjunction with FIG. 5.

In FIG. 6B, the pressure and flow response to Dobutamine infusion is shown. The pulmonary artery flow waveform 76 retains the generally triangular contour 78 but is characterized by a higher peak associated with increased flow in response to Dobutamine infusion. In contrast, the RVP contour 74 is altered considerably compared to the normal RVP contour 60 shown in FIG. 6A. However, the landmark points 82, 84, and 86, which correspond in time to the onset, peak and end of flow, can be extracted from the pressure waveform 74 using the method described above in conjunction with FIG. 5. The landmark points 82, 84, and 86 define a triangular contour 80. The estimated flow contour for the Dobutamine response provided by triangle 80 is increased in height compared to the estimated triangular flow contour 66 for control (FIG. 6A), reflecting the increase in peak flow observed in the Dobutamine response flow waveform 76. Changes in the RVP contour 74, in particular the heightened second shoulder 85, which is expected to be related to an increased afterload and increased wave reflection, do not affect the triangular estimated flow contour 80 based on the extracted landmark points 82, 84 and 86. Thus, a flow contour estimate can be derived from a pressure waveform, independent of afterload and preload related changes to the pressure contour, using extracted points corresponding in time to key features of an actual flow waveform.

Figure 7:
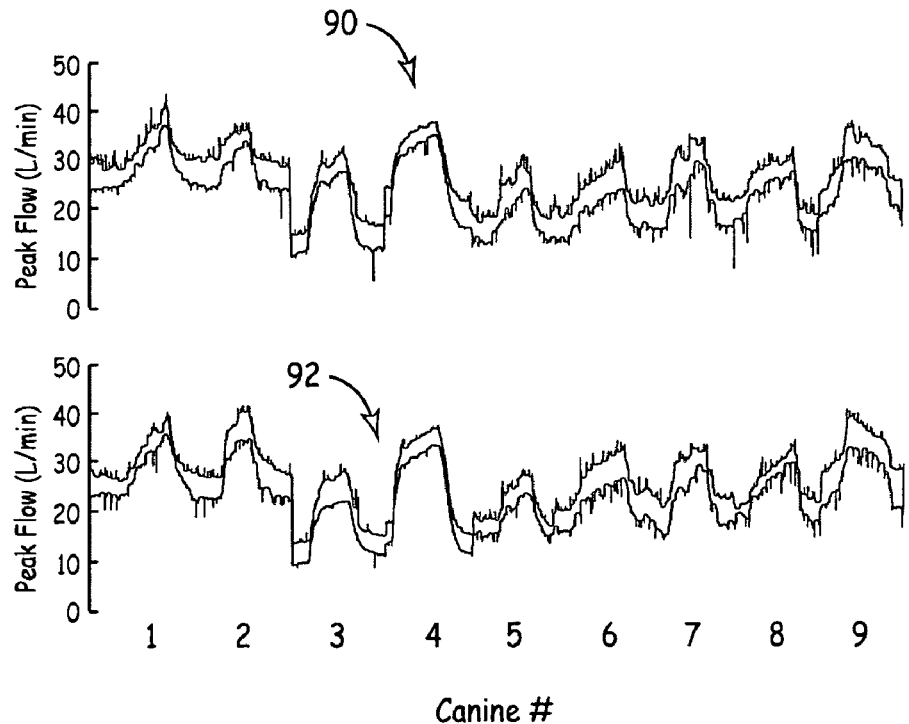
FIG. 7 is a time-based plot showing the beat-by-beat tracking of the actual measured peak pulmonary artery flow by the estimated peak flow during Dobutamine infusion in a canine study (n=9).

FIG. 7 is a time-based plot showing the beat-by-beat tracking of the actual measured peak pulmonary artery flow by the estimated peak flow during Dobutamine infusion in a canine study (n=9). The estimated peak flow is computed from the triangular estimation of the pulmonary artery flow contour using RVP signals. The measured pulmonary artery flow 90 presented an increase in peak flow in response to Dobutamine infusion in all subjects. The estimated peak flow 92 demonstrates that the actual measured flow 90 is well-tracked by the triangular flow contour estimation method.

Figure 8:
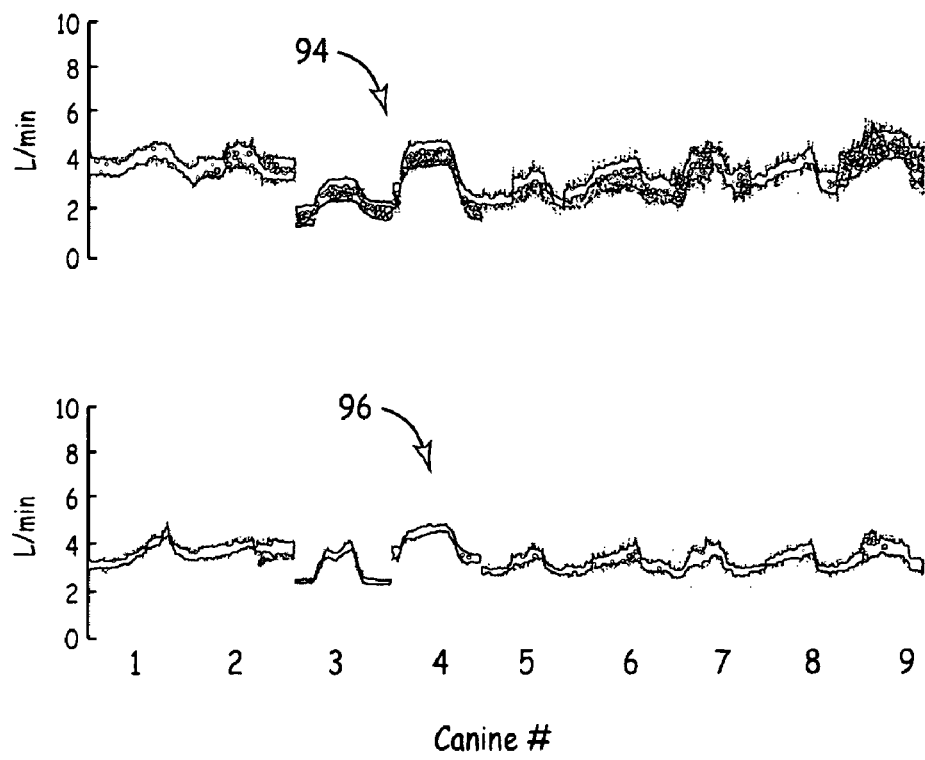
FIG. 8 is a plot of beat-to-beat stroke volume estimated using the flow contour method described herein and the actual measured stroke volume during Dobutamine infusion in a canine study (n=9).

FIG. 8 is a plot of beat-to-beat stroke volume estimated using the flow contour method described herein and the actual measured stroke volume during Dobutamine infusion in a canine study (n=9). Pulmonary flow contour estimation was performed using a right ventricular pressure waveform according to the method described above in conjunction with FIG. 5. The area of the triangular flow contour estimated according to extraction of the three landmark points corresponding to the onset, peak and end of pulmonary artery flow was computed as the estimated stroke volume. The estimated stroke volume 96 tracked well with the Dobutamine response of the actual measured stroke volume 96 in all subjects.

In the exemplary results shown, universal calibration constants were used for all 9 subjects in the study. Individually determined calibration constants can be expected to yield a more accurate estimate of actual stroke volume. The linear regression of the beat-to-beat relationship of the estimated and measured stroke volumes can be used for determining calibration values (a linear gain and offset) for converting the estimated stroke volume in digital units to actual units of volume (ml).

In the exemplary embodiments described herein, the flow contour is approximated as a triangle using a set of three landmark points derived from the pressure waveform. In other embodiments, the flow contour may be approximated using other geometric shapes or combinations of geometric shapes or functions defined by multiple landmark points derived from the pressure waveform. It is further recognized that the process of identifying landmark points on the pressure waveform may involve the analysis of other physiological signals. For example, identifying the time of a particular event during the cardiac cycle at which a landmark pressure point is to be identified may involve sensing events from a wall motion, acoustical, or other mechanical sensor of cardiac function.

The examples provided herein relate to estimation of the flow contour during the systolic portion of the cardiac cycle. However, the methods provided by the present invention may be put to practice for estimating a flow contour during the diastolic portion of the cardiac cycle. For example, landmark points may be identified on a ventricular pressure waveform during diastolic filling to estimate a flow contour corresponding to early diastolic filling, commonly referred to as E-waves during Doppler ultrasound measurements of blood flow.

Thus, a system and method have been described which provide an estimation of a blood flow contour derived from a pressure signal. Aspects of the present invention have been illustrated by the exemplary embodiments described herein. Numerous variations for estimating a flow contour from pressure signals may be conceived by one having skill in the art and the benefit of the teachings provided herein. The described embodiments are intended to be illustrative of methods for practicing the invention and, therefore, should not be considered limiting with regard to the following claims.

What is claimed is:

1. A method of hemodynamic monitoring in an implantable medical device, comprising:
    sensing a blood pressure signal using the implantable medical device;
    extracting a plurality of landmark points on the blood pressure signal corresponding in time to blood flow events using the implantable medical device; and
    deriving a flow contour estimate corresponding to the extracted points using the implantable medical device, wherein the blood pressure signal comprises a ventricular pressure signal.

2. The method of claim 1 wherein extracting a plurality of landmark points comprises identifying a point on the ventricular pressure signal corresponding in time to a maximum peak of a first time derivative of the pressure signal.

3. The method of claim 1 wherein extracting a plurality of landmark points comprises identifying a point on the ventricular pressure signal corresponding in time to a first peak of a third time derivative of the pressure signal.

4. The method of claim 1 wherein extracting a plurality of landmark points comprises identifying a point on the ventricular pressure signal corresponding in time to a minimum peak of the first time derivative of the pressure signal.

5. A method of hemodynamic monitoring in an implantable medical device, comprising:
    sensing a blood pressure signal using the implantable medical device;
    extracting a plurality of landmark points on the blood pressure signal corresponding in time to blood flow events using the implantable medical device; and
    deriving a flow contour estimate corresponding to the extracted points using the implantable medical device, wherein deriving the flow contour estimate comprises deriving a triangle defined by the extracted points.

6. A method of hemodynamic monitoring in an implantable medical device, comprising:
    sensing a blood pressure signal using the implantable medical device;
    extracting a plurality of landmark points on the blood pressure signal corresponding in time to blood flow events using the implantable medical device;
    deriving a flow contour estimate corresponding to the extracted points using the implantable medical device, wherein the flow contour estimate is an approximation of a flow waveform corresponding to the blood pressure signal; and
    computing a stroke volume using the derived flow contour estimate.

7. A system, comprising:
    means for sensing a blood pressure signal;
    means for extracting a plurality of landmark points on the blood pressure signal corresponding in time to blood flow events; and
    means for deriving a flow contour estimate corresponding to the extracted points, wherein the blood pressure signal comprises a ventricular pressure signal, wherein the means for extracting a plurality of landmark points comprises means for identifying a point on the ventricular pressure signal corresponding in time to a maximum peak of a first time derivative of the pressure signal.

8. The method of claim 6, wherein the stroke volume is computed as an area defined by the flow contour estimate.

9. The method of claim 6, wherein extracting the plurality of landmark points comprises identifying points corresponding to at least one of an approximate time of pulmonic valve opening, an approximate time of peak pulmonary artery flow and an approximate time of pulmonic valve closure.

10. The method of claim 9, wherein the stroke volume is computed by the equation SV=0.5*(RVPshoulder−RVPonset)*(Tonset−Tend), wherein RVPshoulder is a RVP (right ventricular pressure) amplitude at the time corresponding to the peak pulmonary artery flow, RVPonset is a RVP amplitude at the point in time corresponding to the pulmonic valve opening, Tonset is the time of the pulmonic valve opening and T(end) is the time of the pulmonic valve closure.

* * * * *